United States Patent
Li et al.

(10) Patent No.: US 12,119,108 B2
(45) Date of Patent: Oct. 15, 2024

(54) MEDICAL ETL TASK DISPATCHING METHOD, SYSTEM AND APPARATUS BASED ON MULTIPLE CENTERS

(71) Applicant: ZHEJIANG LAB, Zhejiang (CN)

(72) Inventors: Jingsong Li, Hangzhou (CN); Wenchao Xiang, Hangzhou (CN); Guangyuan Deng, Hangzhou (CN); Tianshu Zhou, Hangzhou (CN); Yu Tian, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 18/363,701

(22) Filed: Aug. 1, 2023

(65) Prior Publication Data

US 2024/0071607 A1     Feb. 29, 2024

(30) Foreign Application Priority Data

Aug. 31, 2022   (CN) .......................... 202211051570.4

(51) Int. Cl.
    *G06F 16/25*        (2019.01)
    *G06F 9/48*         (2006.01)
    (Continued)

(52) U.S. Cl.
CPC .......... *G16H 40/20* (2018.01); *G06F 9/4881* (2013.01); *G06F 16/254* (2019.01); *G16H 10/60* (2018.01)

(58) Field of Classification Search
CPC ...... G16H 40/20; G16H 10/60; G06F 16/254; G06F 9/4881
(Continued)

(56) References Cited

U.S. PATENT DOCUMENTS

| | | | |
|---|---|---|---|
| 8,954,968 B1 * | 2/2015 | Pohl | G06F 11/3419 |
| | | | 718/103 |
| 2016/0098292 A1 | 4/2016 | Boutin et al. | |
| 2022/0229697 A1 * | 7/2022 | Nakano | G06F 9/4881 |

FOREIGN PATENT DOCUMENTS

| | | |
|---|---|---|
| CN | 105487930 A | 4/2016 |
| CN | 109408236 A | 3/2019 |

(Continued)

OTHER PUBLICATIONS

Notice Of Allowance(CN202211051570.4); Date of Mailing: Nov. 10, 2022.
(Continued)

*Primary Examiner* — Robert W Beausoliel, Jr.
*Assistant Examiner* — Lauren Zannah Ganger
(74) *Attorney, Agent, or Firm* — W&G Law Group

(57) ABSTRACT

The present disclosure discloses a medical ETL task dispatching method, system and apparatus based on multiple centers. The method includes following steps: step S1: testing and verifying ETL tasks; step S2: deploying the ETL tasks to a hospital center, and dispatching the ETL tasks to a plurality of executors for execution; step S3: screening an executor set meeting resource demands of ETL tasks to be dispatched; step S4: calculating a current task load of each executor in the executor set; step S5: selecting the executor with a minimum current task load to execute the ETL tasks; and step S6: selecting, by the dispatching machine, the ETL tasks from executor active queues according to a priority for execution. The present disclosure selects the most suitable executor by analyzing a serving index as a task to be dispatched on a current dispatching machine.

8 Claims, 4 Drawing Sheets

(51) Int. Cl.
*G16H 10/60* (2018.01)
*G16H 40/20* (2018.01)

(58) Field of Classification Search
USPC .......................................................... 707/602
See application file for complete search history.

(56) References Cited

FOREIGN PATENT DOCUMENTS

| | | | |
|---|---|---|---|
| CN | 110287245 A | 9/2019 |
| CN | 113687938 A | 11/2021 |
| CN | 113778646 A | 12/2021 |
| CN | 114518945 A | 5/2022 |

OTHER PUBLICATIONS

First Office Action(CN202211051570.4); Date of Mailing: Oct. 21, 2022.
One-Scheduling-Method-for-ETL-Task-Cluster.
PBS An-ETL-Scheduling-Algorithm-for-Cluster-Environment.
Optimization-of-regional-medical-data-collection-methods(machine translation).
Research-on-distributed-ETL-tasks-scheduling-strategy-based-on-ISE-algorithm.

* cited by examiner

MEDICAL ETL TASK DISPATCHING METHOD, SYSTEM AND APPARATUS BASED ON MULTIPLE CENTERS

CROSS-REFERENCE TO RELATED APPLICATIONS

The present application claims priority to Chinese Patent Application No. 202211051570.4, filed on Aug. 31, 2022, the content of which is incorporated herein by reference in its entirety.

TECHNICAL FIELD

The present disclosure relates to the technical field of medical data ETL, in particular to a medical ETL task dispatching method, system and apparatus based on multiple centers.

BACKGROUND

ETL (Extract-Transform-Load) is used to describe a process of extracting, transforming and loading data from a source end to a destination end, and aims to integrate scattered and disorderly data with inconsistent standards in an organization, so as to realize further mining and utilization of the data and provide a basis for the decision analysis of the organization.

Medical ETL refers to an ETL process applied to hospitals. In recent years, hospital informatization has developed rapidly, with the establishment of various hospital business systems, massive medical related data have been generated, and how to realize mining and processing of these data is of great significance for the hospitals and related research institutions. At the same time, a multi-center model, which utilizes data from a plurality of medical institutions for collaborative analysis and research, is also a trend in the industry. In order to realize ETL processing of massive multi-center medical data, a large number of ETL tasks need to be established. However, machine performance in the medical institutions is usually limited and cannot support a large number of computing tasks. Therefore, a common scheme is to send the ETL tasks to a cluster environment for dispatching and execution.

An execution process of the medical ETL tasks is usually divided into a plurality of closely related sub-stages, each sub-stage has a sequential dependence relationship, and some intermediate results will be generated and used. Therefore, in order to facilitate design and implementation of the tasks, the plurality of sub-stages are usually executed as a whole task. Each of these sub-stages executes a design logic, for example, the first stage is responsible for processing related to mathematical calculation, and the second stage is responsible for processing related to deep learning, etc. In general, a single stage has a large dependence on a certain machine resource (such as a CPU, a GPU, and a memory), however, different stages of the same task may have different dependences on the machine resource. At the same time, the cluster executing the task is usually a heterogeneous cluster, resource performance between machines is different, and different machines may have different adaptabilities to different tasks and different stages of the same task. Therefore, in order to maximize the utilization of the resources of the heterogeneous cluster and improve the overall dispatching performance of the multi-stage tasks, it is necessary to take full advantage of the features of the medical ETL tasks and the cluster machines.

Currently, in most cases, an existing medical data ETL system does not distinguish demand differences, for the machine resource, of the task in different stages, nor does the medical data ETL system combine information such as the resource characteristics and task loads of the machines in the heterogeneous cluster for dynamic dispatching. Under the scenario of clustered ETL task dispatching in a plurality of hospitals, the present disclosure aims to maximize the utilization of cluster resources and improve the throughput of cluster operation by constructing a two-level dispatching mechanism, including a dispatching machine and an executor, in view of the characteristics of the plurality of stages of the tasks.

SUMMARY

In order to solve the above technical problem, the present disclosure provides a medical ETL task dispatching method, system and apparatus based on multiple centers.

A technical solution adopted by the present disclosure is as follows:

a medical ETL task dispatching method based on multiple centers includes following steps:
step S1: generating ETL tasks, collecting resource demands of the ETL tasks and determining a time prediction equation by using a test machine, and testing and verifying the ETL tasks;
step S2: deploying the ETL tasks to a hospital center, and dispatching, by the hospital center, the ETL tasks to a plurality of executors through a dispatching machine for execution;
step S3: collecting and counting up, by the dispatching machine, resource index vectors reported by each executor and resource demand vectors of ETL tasks to be dispatched in a current stage, and screening an executor set meeting resource demands of the ETL tasks to be dispatched;
step S4: calculating a current task load of each executor in the executor set;
step S5: selecting, by the dispatching machine, the executor with a minimum current task load to execute the ETL tasks according to the current task load of each executor; and
step S6: adding, by the dispatching machine, the ETL tasks to executor active queues, determining a priority of the ETL tasks in the executor active queues according to prediction time determined by the prediction equation, and selecting, by the dispatching machine, the ETL tasks from the executor active queues according to the priority for execution.

Furthermore, step S1 specifically includes following sub-steps:
step S11: generating the ETL tasks, operating the ETL tasks through the test machine, dividing data in an ETL task operating process into test data and verification data, and respectively collecting resource demands of the test data and resource demands of the verification data;
step S12: reading a data volume and a data reading rate of the test data by using the test machine, and determining the time prediction equation according to the data volume and the data reading rate;
step S13: obtaining prediction time of the ETL tasks corresponding to the test data by using the time prediction equation; and
step S14: verifying the resource demands and the prediction time, and when the resource demands of the test data meet the resource demands of the verification data, and meanwhile, a difference value between the prediction time and actual execution time of the ETL tasks corresponding to the verification data is less than a preset threshold value, completing test and verification of the ETL tasks.

Furthermore, step S2 specifically includes following sub-steps:
step S21: deploying the ETL tasks to the hospital center;
step S22: determining the prediction time of the ETL tasks by using the time prediction equation;
step S23: determining the priority of the ETL tasks by using the prediction time; and
step S24: dispatching, by the dispatching machine, the ETL tasks to the executors for execution according to the priority of the ETL tasks.

Furthermore, step S22 specifically includes using the time prediction equation to determine the prediction time of the ETL tasks through the number of ETL tasks remaining to be processed in the current stage and the data reading rate of the hospital center.

Furthermore, step S24 specifically includes following sub-steps:
step S241: initiating, by the dispatching machine, active task queues and expired task queues;
step S242: adding the ETL tasks to the active task queues according to the priority; and
step S243: when the ETL tasks in the active task queues are empty, exchanging the active task queues and the expired task queues, and continuously performing, by the dispatching machine, distributing and dispatching from the active task queues.

Furthermore, step S3 specifically includes following sub-steps:
step S31: collecting and counting up, by the dispatching machine, resource index vectors of any executor;
step S32: collecting and counting up, by the dispatching machine, the resource demand vectors of the ETL tasks to be dispatched in the current stage; and
step S33: screening the executor set meeting the resource demands of the ETL tasks to be dispatched by using the resource index vectors and the resource demand vectors.

Furthermore, step S4 specifically includes following sub-steps:
step S41: calculating a sum of prediction time of all the ETL tasks in each executor active queue and each executor expire queue in each executor set by using the time prediction equation; and
step S42: calculating current task loads corresponding to the executors through the sum of the prediction time and a collection of all the ETL tasks.

Furthermore, when the current task loads of the plurality of executors are the same in step S5, the executor with a minimum value is screened out to perform dispatching and execution on the ETL tasks according to the resource index vectors of the executors in the current stage and the resource demand vectors of the ETL tasks in the current stage in combination with resource weight values of the executors.

Furthermore, when the plurality of executors are still screened out in step S5, one executor is randomly selected to perform dispatching and execution on the ETL tasks.

Furthermore, in the ETL task execution process of step S6, an ETL task operation time threshold value is set, when the ETL task execution time is greater than or equal to the ETL task operation time threshold value, execution of the ETL tasks is paused, and the ETL tasks are added to the executor expire queues for waiting for next-time dispatching.

Furthermore, in the ETL task execution process of step S6, ETL task stage information is detected, when stages are switched, execution of the ETL tasks is paused, and the ETL tasks are added to the expired task queues of the dispatching machine for waiting for re-dispatching by the dispatching machine.

Furthermore, in the ETL task execution process of step S6, when executor active queues are empty after executor dispatching, the executor active queues and the executor expire queues are exchanged, and the dispatching machine continuously performs dispatching execution from the executor active queues.

The present disclosure further provides a medical ETL task dispatching system based on multiple centers, including:
a test module, configured to collect ETL task operation data and determine resource demands of ETL tasks and a time prediction equation;
a hospital center module, configured to deploy the ETL tasks and submit the ETL tasks to a dispatching machine module to perform dispatching and distributing of the ETL tasks;
the dispatching machine module, configured to calculate executor sources and task loads, to calculate task prediction time to determine a priority of the ETL tasks by using the time prediction equation, and to dispatch the ETL tasks to an executor module according to the priority; and
the executor module, configured to execute the ETL tasks and perform overtime dispatching and stage switching dispatching on the ETL tasks.

The present disclosure further provides a medical ETL task dispatching apparatus based on multiple centers, including a memory and one or more processors, wherein the memory stores an executor code, and when executing the executable code, the one or more processors are configured to implement the medical ETL task dispatching method based on the plurality of centers according to any one of the above embodiments.

The present disclosure further provides a computer readable storage medium, wherein a program is stored on the computer readable storage medium, and when the program is executed by a processor, the medical ETL task dispatching method based on the plurality of centers according to any one of the above embodiments is implemented.

The beneficial effects of the present disclosure are: the present disclosure analyzes the resource demands, a data processing speed and other indexes of each stage of the tasks by counting up operation data of each stage of the tasks on the test machine. A cluster machine is divided into one dispatching machine and the plurality of executors. Both the dispatching machine and the executors are designed with execution queues and waiting queues. The dispatching machine is only responsible for dispatching work. The dispatching machine dispatches the tasks submitted by the plurality of centers to the executors for execution. The dispatching machine monitors the resource indexes of the cluster executors and the loads of queued tasks on the executors in real time, and selects the most suitable executor for the tasks to be dispatched on the current dispatching machine. The executors select the tasks from the execution queues for execution, and meanwhile, to prevent a certain task from occupying the machine resource for a long time, the dispatching machine dispatches the tasks back to the expire queues of the current executors after the specified time is used up, and selects a new task from the active queues for execution. At the same time, in order to take full advantage of the different stage characteristics of the tasks and the cluster resource situation, when executing the tasks, the executors will monitor the stage information of the current tasks. When stage switching occurs, the tasks are dispatched back to the dispatching machine and wait for being re-dispatched to the appropriate executor for operation, thereby realizing maximization of the utilization of the cluster resources.

DESCRIPTION OF EMBODIMENTS

The following description of at least one exemplary embodiment is in fact illustrative only and never acts as any limitation on the present disclosure and its application or use. Based on the embodiments of the present disclosure, all other embodiments obtained by those ordinarily skilled in the art without creative labor fall within the scope of protection of the present disclosure.

Figure 1:
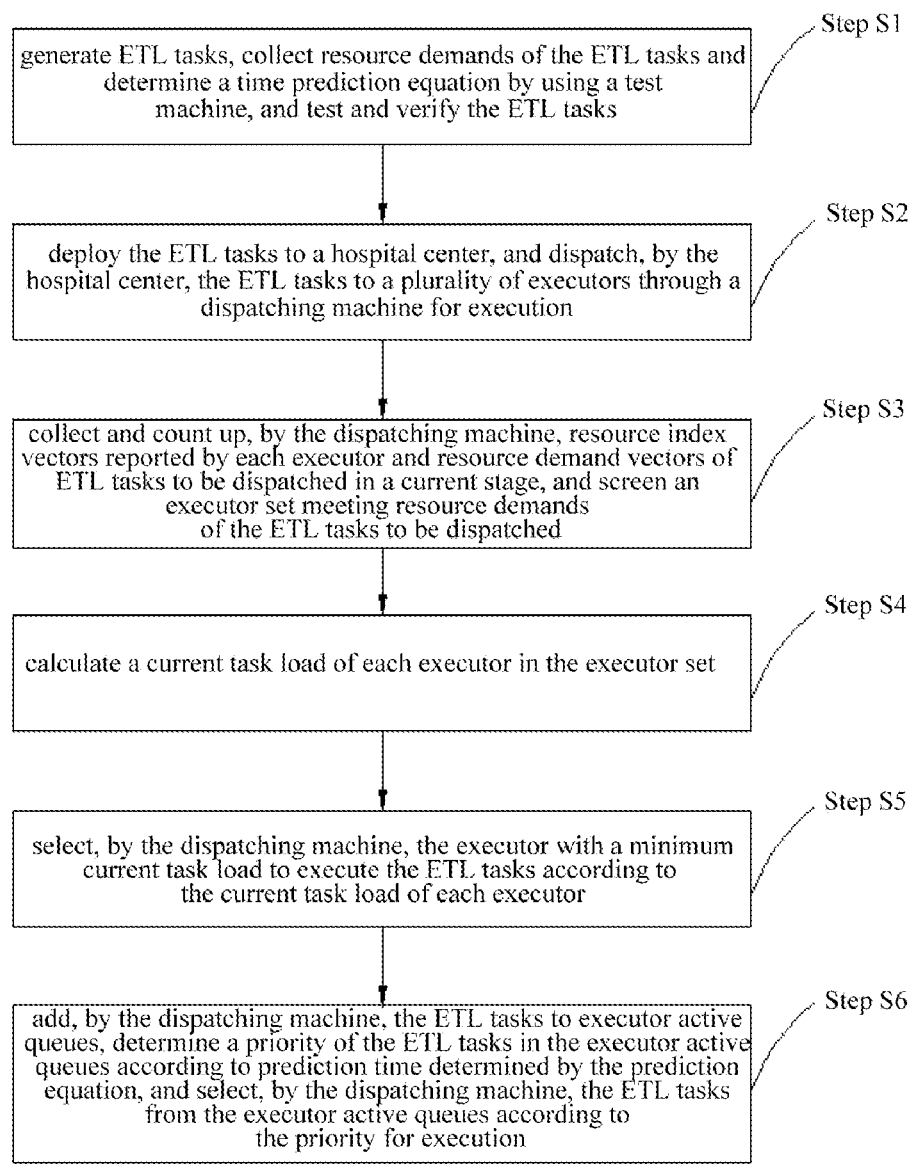
FIG. 1 is a flow diagram of a medical ETL task dispatching method based on multiple centers of the present disclosure.

Referring to FIG. 1, a medical ETL task dispatching method based on multiple centers includes following steps:

step S1: ETL tasks are generated, a test machine is used to collect resource demands of the ETL tasks and determine a time prediction equation, and the ETL tasks are tested and verified;

step S11: the ETL tasks are generated, the ETL tasks are operated through the test machine, data in an ETL task operating process are divided into test data and verification data, and resource demands of the test data and resource demands of the verification data are respectively collected;

step S12: the test machine is used to read a data volume and a data reading rate of the test data, and the time prediction equation is determined according to the data volume and the data reading rate;

step S13: the time prediction equation is used to obtain prediction time of the ETL tasks corresponding to the test data; and step S14: the resource demands and the prediction time are verified, and when the resource demands of the test data meet the resource demands of the verification data, and meanwhile, a difference value between the prediction time and actual execution time of the ETL tasks corresponding to the verification data is less than a preset threshold value, test and verification of the ETL tasks are completed.

Step S2: the ETL tasks are deployed to a hospital center, and the hospital center dispatches the ETL tasks to a plurality of executors through a dispatching machine for execution;

step S21: the ETL tasks are deployed to the hospital center;

step S22: the time prediction equation is used to determine the prediction time of the ETL tasks; and the time prediction equation is used to determine the prediction time of the ETL tasks specifically includes that the time prediction equation is used to determine the prediction time of the ETL tasks through the number of ETL tasks remaining to be processed in the current stage and the data reading rate of the hospital center.

Step S23: the prediction time is used to determine a priority of the ETL tasks; and step S24: the ETL tasks are dispatched to the executors for execution by the dispatching machine according to the priority of the ETL tasks.

Step S241: the dispatching machine initiates active task queues and expired task queues;

step S242: the ETL tasks are added to the active task queues according to the priority; and step S243: when the ETL tasks in the active task queues are empty, the active task queues and the expired task queues are exchanged, and the dispatching machine continuously performs distributing and dispatching from the active task queues.

Step S3: the dispatching machine collects and counts up resource index vectors reported by each executor and resource demand vectors of ETL tasks to be dispatched in a current stage, and screens an executor set meeting resource demands of the ETL tasks to be dispatched;

step S31: the dispatching machine collects and counts up the resource index vectors of any executor;

step S32: the dispatching machine collects and counts up the resource demand vectors of the ETL tasks to be dispatched in the current stage; and step S33: the resource index vectors and the resource demand vectors are used to screen the executor set meeting the resource demands of the ETL tasks to be dispatched.

Step S4: a current task load of each executor in the executor set is calculated;

step S41: the time prediction equation is used to calculate a sum of prediction time of all the ETL tasks in each executor active queue and each executor expire queue in each executor set; and step S42: current task loads corresponding to the executors are calculated through the sum of the prediction time and a collection of all the ETL tasks.

Step S5: the dispatching machine selects the executor with a minimum current task load to execute the ETL tasks according to the current task load of each executor; and when the current task loads of the plurality of executors are the same, the executor with a minimum value is screened out to perform dispatching and execution on the ETL tasks according to the resource index vectors of the executors in the current stage and the resource demand vectors of the ETL tasks in the current stage in combination with resource weight values of the executors.

When the plurality of executors are still screened out, one executor is randomly selected to perform dispatching and execution on the ETL tasks.

Step S6: the dispatching machine adds the ETL tasks to executor active queues, a priority of the ETL tasks in the executor active queues is determined according to prediction time determined by the prediction equation, and the dispatching machine selects the ETL tasks from the executor active queues according to the priority for execution.

In the ETL task execution process, an ETL task operation time threshold value is set, when the ETL task execution time is greater than or equal to the ETL task operation time threshold value, execution of the ETL tasks is paused, and the ETL tasks are added to executor expire queues, and wait for next-time dispatching.

In the ETL task execution process, ETL task stage information is detected, when stages are switched, execution of the ETL tasks is paused, and the ETL tasks are added to the expired task queues of the dispatching machine, and wait for re-dispatching by the dispatching machine.

In the ETL task execution process, when the executor active queues are empty after executor dispatching, the executor active queues and the executor expire queues are exchanged, and the dispatching machine continuously performs dispatching execution from the executor active queues.

Figure 2:
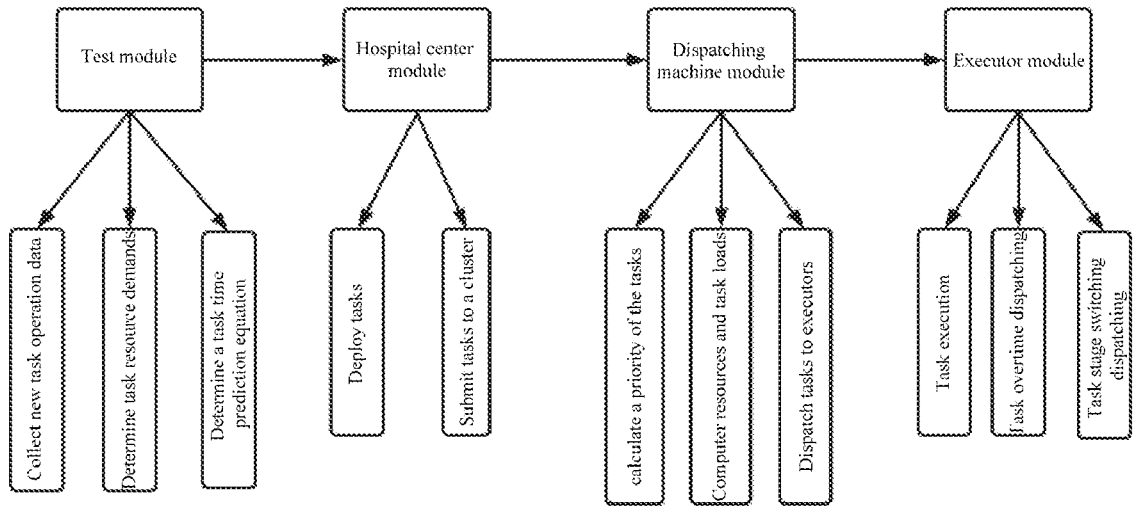
FIG. 2 is a structural diagram of a medical ETL task dispatching system based on multiple centers of the present disclosure.

Referring to FIG. 2, a medical ETL task dispatching system based on multiple centers includes:
- a test module, configured to collect ETL task operation data and determine resource demands of ETL tasks and a time prediction equation;
- a hospital center module, configured to deploy the ETL tasks and submit the ETL tasks to a dispatching machine module to perform dispatching and distributing of the ETL tasks;
- the dispatching machine module, configured to calculate executor sources and task loads, use the time prediction equation to calculate task prediction time to determine a priority of the ETL tasks and dispatch the ETL tasks to an executor module according to the priority; and
- the executor module, configured to execute the ETL tasks and perform overtime dispatching and stage switching dispatching on the ETL tasks.

Figure 3:
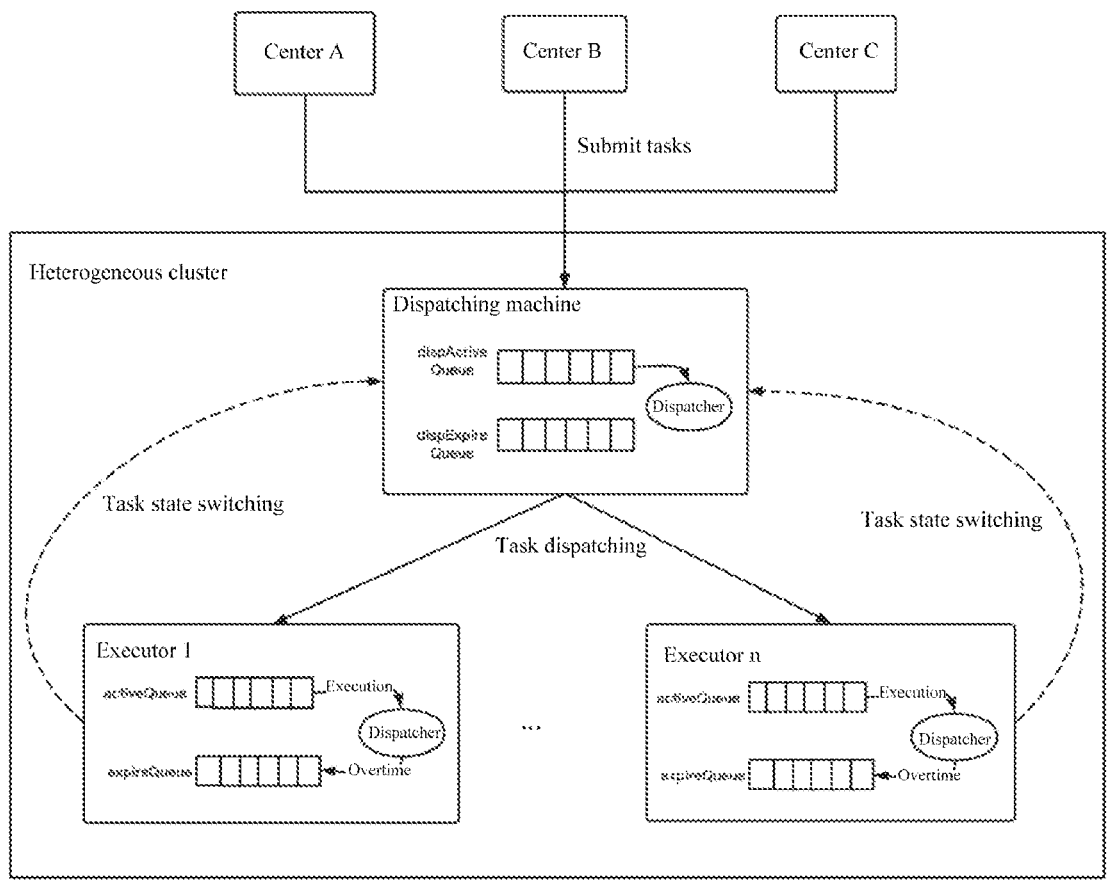
FIG. 3 is a system architecture diagram of an embodiment of the present disclosure.
Figure 4:
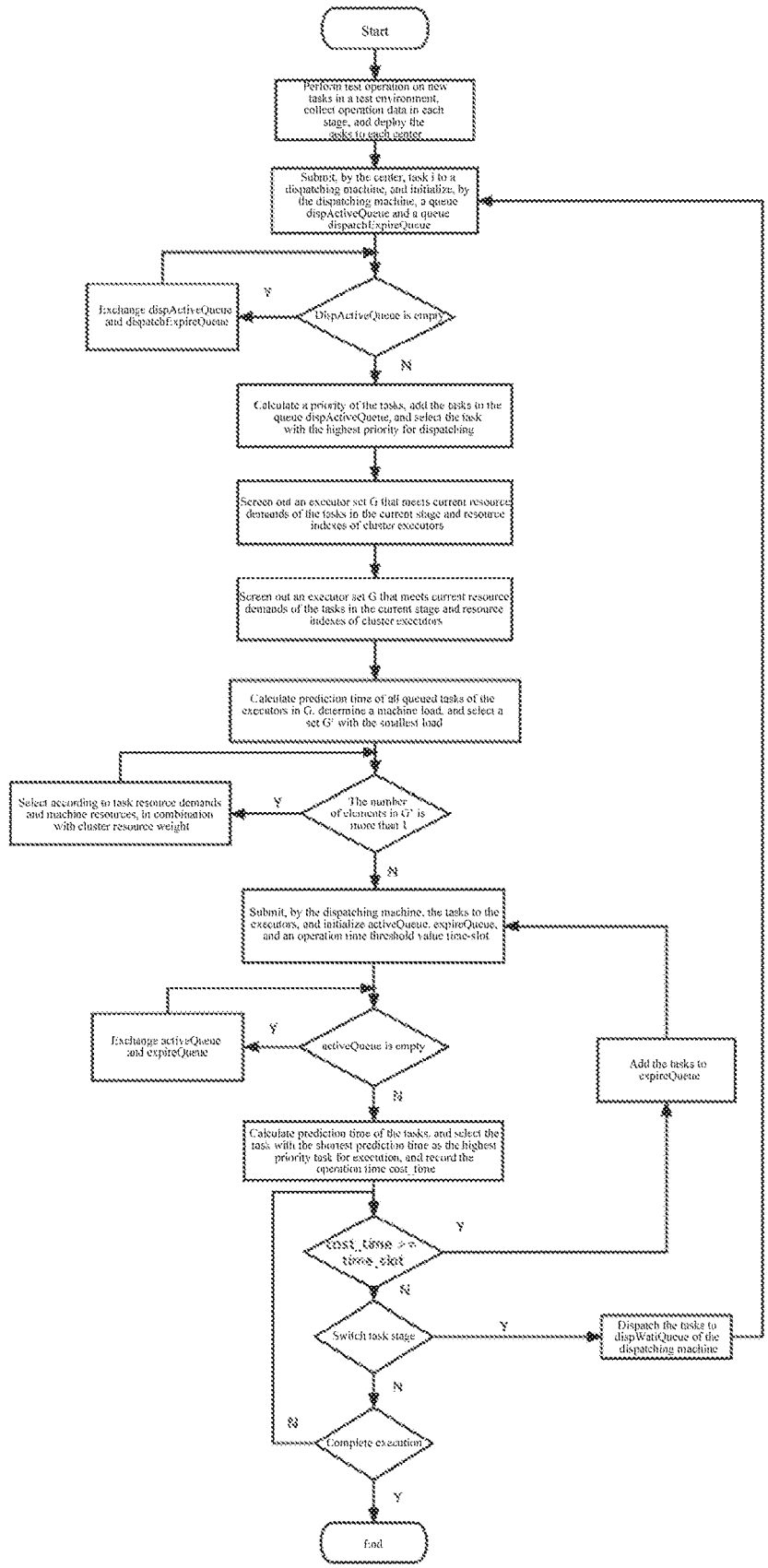
FIG. 4 is a flow diagram of a multi-stage task dispatching strategy of an embodiment of the present disclosure.

Embodiment, referring to FIG. 3 to FIG. 4:
step S1: ETL tasks are generated, a test machine is used to collect resource demands of the ETL tasks and determine a time prediction equation, and the ETL tasks are tested and verified; and after a multi-stage ETL task $Task_i$ is developed and before the multi-stage ETL task $Task_i$ is deployed to a hospital center, test operation of a plurality of simulation data needs to be performed in a test environment. In a simulation test stage, demand information of the tasks for machine resources in different stages is collected on the test machine, wherein the machine resources include CPU, GPU and memory resources.

Step S11: the ETL tasks are generated, the ETL tasks are operated through the test machine, data in an ETL task operating process are divided into test data and verification data, and resource demands of the test data and resource demands of the verification data are respectively collected; and step S12: the test machine is used to read a data volume and a data reading rate of the test data, and the time prediction equation $PRE\_T_i^k$ is determined according to the data volume and the data reading rate:

$$PRE\_T_i^k = a\frac{V_k}{I_k} + b$$

where, $V_k$ represents a data volume, to be processed, of the ETL task $Task_i$ in a stage k, $I_k$ represents the data reading rate, and a and b are constant indexes.

Step S13: the time prediction equation is used to obtain prediction time of the ETL tasks corresponding to the test data; and required resources and prediction equation parameters a and b are obtained by executing data of a collection part, and the time prediction equation is used to obtain the prediction time of the ETL tasks.

Step S14: the resource demands and the prediction time are verified, and when the resource demands of the test data meet the resource demands of the verification data, and meanwhile, a difference value between the prediction time and actual execution time of the ETL tasks corresponding to the verification data is less than a preset threshold value, test and verification of the ETL tasks are completed.

Step S2: the ETL tasks are deployed to a hospital center, and the hospital center dispatches the ETL tasks to a plurality of executors through a dispatching machine for execution;
- step S21: the ETL tasks are deployed to the hospital center;
- step S22: the time prediction equation is used to determine the prediction time of the ETL tasks; and
- a prediction time calculation method uses the time prediction equation $PRE\_T_i^k$, and calculation is completed through the data volume $V_k$ remaining to be processed of the ETL task $Task_i$ in the current stage k and the data reading rate $I_k$ of the current hospital center.

The method specifically includes that the time prediction equation is used and the prediction time of the ETL tasks is determined through the number of ETL tasks remaining to be processed in the current stage and the data reading rate of the hospital center.

Step S23: the prediction time is used to determine a priority of the ETL tasks; and in the present disclosure, a shortest task priority principle is used to determine the priority, and it is stipulated that the task with the shorter remaining processing time in the current stage has a higher priority to reduce the average waiting time of all tasks.

Step S24: the ETL tasks are dispatched to the executors for execution by the dispatching machine according to the priority of the ETL tasks.

Step S241: the dispatching machine initiates active task queues dispActiveQueue and expired task queues dispExpireQueue;
- step S242: the ETL tasks are added to the active task queues according to the priority; and
- step S243: when the ETL tasks in the active task queues are empty, the active task queues dispActiveQueue and the expired task queues dispExpireQueue are exchanged, and the dispatching machine continuously performs distributing and dispatching from the active task queues.

Step S3: the dispatching machine collects and counts up resource index vectors reported by each executor and resource demand vectors of ETL tasks to be dispatched in a current stage, and screens an executor set meeting resource demands of the ETL tasks to be dispatched;
- step S31: the dispatching machine collects and counts up the resource index vectors of any executor;
- the executors are represented by S [S1, S2, ..., Sj, ... Sm], and for any executor Sj, the resource index vectors are represented by Sj [$R_{j,cpu}$, $R_{j,gpu}$, $R_{j,mem}$], representing indexes of the CPU, GPU and memory resources of the executor;

step S32: the dispatching machine collects and counts up the resource demand vectors of the ETL tasks to be dispatched in the current stage; and the resource demand vectors of the ETL tasks i to be dispatched in the current stage k are $D_i^k[D_{i,cpu}^k, D_{i,gpu}^k, D_{i,mem}^k]$.

Step S33: the resource index vectors and the resource demand vectors are used to screen the executor set G={S1, S2, ..., Sn} meeting the resource demands of the ETL tasks to be dispatched.

$$G_j = \begin{cases} S_j, \sum_{res \in RE} \frac{R_{j,res}}{D_{i,res}^k} = 3, \max \frac{R_{j,res}}{D_{i,res}^k} = 1 & , j \in S, RE = \{cpu, gpu, mem\} \\ 0, \text{others} \end{cases}$$

where, $R_{j,res}$ represents a res resource index of an executor j, $D_{i,res}^k$ represents a res resource demand of the task i in the stage k, and when $$D_{i,res}^k = 0, \frac{R_{j,res}}{D_{i,res}^k} \text{ is } 1.$$

$G_j$ being 0 represents that the current executor j is not added to the executor set G.

Step S4: a current task load of each executor in the executor set is calculated;

step S41: the time prediction equation is used to calculate a sum of prediction time of all the ETL tasks in each executor active queue activeQueue and each executor expire queue expireQueue in the executor set; and the sum of the prediction time of all the ETL tasks in each executor active queue activeQueue=[T1, T2, ..., Ta] and each executor expire queue expireQueue=[T1, T2, ..., Tw] is calculated, and a task load condition of the executor j is represented as:

step S42: current task loads corresponding to the executors are calculated through the sum of the prediction time and a collection of all the ETL tasks.

$$P_j = \sum_{i \in L}\left(PRE\_T_i^k = a\frac{V_k}{I_k} + b\right) L = activeQueue \cup expireQueue, j \in G$$

where, L is the collection of the tasks in the active queue activeQueue and the expire queue expireQueue in each executor, and $PRE\_T_i^k$ is the time prediction equation, representing prediction remaining time of the $Task_i$ in the ETL tasks in the current stage k according to the remaining data volume $V_k$ in the current stage and a specific data reading rate $I_k$ of the current hospital center, and a and b are constant indexes, and are determined in the task operation data collection stage.

Step S5: the dispatching machine selects the executor with a minimum current task load to execute the ETL tasks according to the current task load of each executor; and according to the current task loads of the executors in the executor set G, a following formula is used for selecting the executor with the minimum current task load for executing the task I;

$$MV_{i,j} = \max\left(\frac{\alpha}{P_j} + \beta\right), j \in G$$

where, a and b are constant factors.

When the current task loads of the plurality of executors are the same, it is represented as a set $\acute{G}$, the executor with a minimum value is screened out to perform dispatching and execution on the ETL tasks according to the resource index vectors Sj $[R_{j,cpu}, R_{j,gpu}, R_{j,men}]$ of the executors in the current stage and the resource demand vectors $D_i^k[D_{i,cpu}^k, D_{i,gpu}^k, D_{i,mem}^k]$ of the ETL tasks in the current stage in combination with resource weight w={$w_{cpu}, w_{gpu}, w_{mem}$} values of the executors:

$$\min\left(\sum_{res \in RE} w_{res} \frac{R_{j,res}}{D_{i,res}^k}\right), RE = \{cpu, gpu, mem\}, j \in \acute{G}$$

where, when $D_{i,res}^k$ is equal to 0, $D_{j,res}/D_{i,res}^k = R_{j,res}$. $w_{cpu} + w_{gpu} + w_{mem}$ is equal to 1, $w_{cpu}$, $w_{gpu}$ and $w_{mem}$ are greater than or equal to 0 and less than or equal to 1, respectively representing weights of the CPU, GPU and memory resources in a current executor cluster, initial values are respectively 0.4, 0.4 and 0.2 according to priori values of the current cluster, and adjustment may be performed according to specific conditions of the executer cluster.

When the plurality of executors are still screened out, one executor is randomly selected to perform dispatching and execution on the ETL tasks.

Step S6: the dispatching machine adds the ETL tasks to the executor active queues activeQueue, a priority of the ETL tasks in the executor active queues activeQueue is determined according to prediction time determined by the prediction equation, and the dispatching machine selects the ETL tasks from the executor active queues activeQueue according to the priority for execution.

The same as the dispatching machine queues, the priority is determined according to the prediction remaining time of the tasks in the current stage, and a time calculation method is the same as the task time prediction equation $PRE\_T_i^k$.

In the ETL task execution process, an ETL task operation time threshold value time_slot is set, when the ETL task execution time cost_time is greater than or equal to the ETL task operation time threshold value time_slot, execution of the ETL tasks is paused, and the ETL tasks are added to the executor expire queues, and wait for next-time dispatching.

The dispatching machine selects new tasks with a highest priority from the expired task queues dispExpireQueu for execution. Through the mechanism, a certain task is prevented from occupying computing resources.

In the ETL task execution process, ETL task stage information is detected, when stages are switched, execution of the ETL tasks is paused, and the ETL tasks are added to the expired task queues dispExpireQueue of the dispatching machine, and wait for re-dispatching by the dispatching machine, and the dispatching machine selects the most suitable executor for dispatching operation according to resource demand characteristics of the tasks in a new stage.

In the ETL task execution process, when the executor active queues activeQueue are empty after executor dispatching, the executor active queues activeQueue and executor expire queues expireQueue are exchanged, and the dispatching machine continuously performs dispatching execution from the executor active queues activeQueue.

In conclusion, based on the demand difference of computing node resources in different stages of the ETL tasks, the present disclosure dispatches the current tasks to the most suitable executor for operation by analyzing the task resource demand and calculating the resource indexes of the executors in the cluster, and meanwhile combining the real-time task load information of the executors, the own multi-stage characteristics of the ETL tasks and computing machine resources are effectively used, execution efficiency of the multi-stage tasks in a heterogeneous cluster is improved, and the throughput of a clustered ETL task dispatching system is improved.

Corresponding to the embodiment of the above medical ETL task dispatching method based on the plurality of centers, the present disclosure further provides an embodiment of a medical ETL task dispatching apparatus based on multiple centers.

Figure 5:
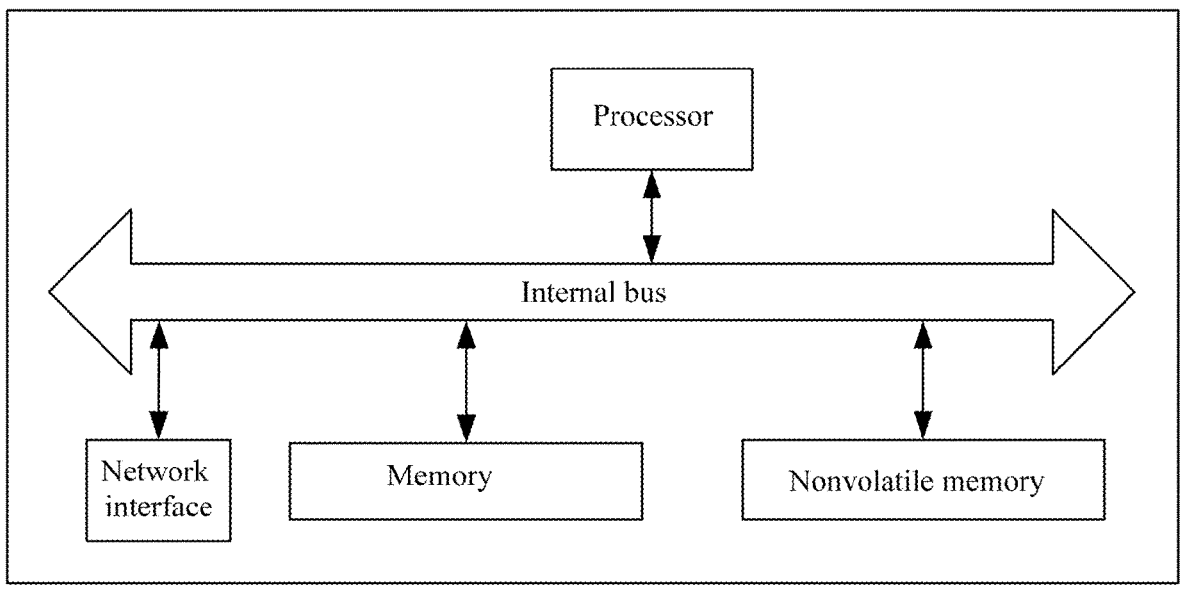
FIG. 5 is a structural diagram of a medical ETL task dispatching apparatus based on multiple centers of the present disclosure.

Referring to FIG. 5, a medical ETL task dispatching apparatus based on multiple centers provided by an embodiment of the present disclosure includes a memory and one or more processors, an executable code is stored in the memory, and when executing the executable code, the one or more processors are configured to implement the medical ETL task dispatching method based on the plurality of centers in the above embodiment.

The embodiment of the medical ETL task dispatching device based on the plurality of centers can be applied to any device with data processing capability, and the device with data processing capability may be a device or apparatus such as a computer. The apparatus embodiment can be realized by software, or hardware or a combination of hardware and software. Taking implementation by the software as an example, as a logical apparatus, the apparatus is formed by reading corresponding computer program instructions in a non-volatile memory into the memory by the processor of any device with data processing capability. In terms of the hardware, FIG. 5 is a hardware structural diagram of any device with data processing capability where the medical ETL task dispatching apparatus based on the plurality of centers is located. In addition to the processor, the memory, a network interface and the non-volatile memory shown in FIG. 5, any device with data processing capability where the apparatus in the embodiment is located may further include other hardware generally according to actual functions of any device with data processing capability, which is not repeated here.

The realization process of the functions and roles of each unit in the above apparatus is detailed in the realization process of the corresponding steps in the above method, which is not repeated here.

For the apparatus embodiments, as the apparatus embodiments basically correspond to the method embodiments, relevance refers to the partial description of the method. The apparatus embodiments described above are only schematic, wherein units described as separate parts may be or may not be physically separate, and components shown as units may be or may not be physical units, that is, located in one place or distributed to a plurality of network units. Part or all of the modules can be selected according to the actual needs to realize the purpose of the scheme of the present disclosure. Those ordinarily skilled in the art may understand and implement the embodiments without creative labor.

An embodiment of the present disclosure further provides a computer readable storage medium, on which a program is stored, and when the program is executed by the processor, the medical ETL task dispatching method based on the plurality of centers in the embodiment is implemented.

The computer readable storage medium may be an internal storage unit, such as a hard disk or memory, of any device with data processing capability described in any of the preceding embodiments. The computer readable storage medium may also be an external storage device of any device with data processing capability, such as a plug-in hard disk, a smart media card (SMC), an SD Card, and a flash card, equipped with the device. Further, the computer readable storage medium may also include both the internal storage unit and the external storage device of any device with the data processing capability. The computer readable storage medium is configured to store the computer program and other programs and data required by any device with data processing capability, and may also be configured to temporarily store data that have been output or are to be output.

The following description of at least one exemplary embodiment is in fact illustrative only and never acts as any limitation on the present disclosure and its application or use. Based on the embodiments of the present disclosure, all other embodiments obtained by those ordinarily skilled in the art without creative labor fall within the scope of protection of the present disclosure

What is claimed is:

1. A medical ETL task dispatching method based on multiple centers, comprising steps of:
step S1: generating ETL tasks, collecting resource demands of the ETL tasks and determining a time prediction equation by using a test machine, and testing and verifying the ETL tasks;
step S11: generating the ETL tasks, operating the ETL tasks through the test machine, dividing data in an ETL task operating process into test data and verification data, and collecting resource demands of the test data and resource demands of the verification data, respectively;
step S12: reading a data volume and a data reading rate of the test data by using the test machine, and determining the time prediction equation $PRE\_T_i^k$ according to the data volume and the data reading rate;

$$PRE\_T_i^k = a\frac{V_k}{I_k} + b$$

wherein $V_k$ represents a data volume, to be processed, of an ETL task $Task_i$ in a stage k, $I_k$ represents the data reading rate, and a and b are constant indexes;
step S13: obtaining prediction time of the ETL tasks corresponding to the test data by using the time prediction equation;
step S14: verifying the resource demands and the prediction time, and when the resource demands of the test data meet the resource demands of the verification data, and meanwhile, a difference value between the prediction time and actual execution time of the ETL tasks corresponding to the verification data is less than a preset threshold value, completing test and verification of the ETL tasks;
step S2: deploying the ETL tasks to a hospital center, and dispatching, by the hospital center, the ETL tasks to a plurality of executors through a dispatching machine for execution;
step S21: deploying the ETL tasks to the hospital center;
step S22: determining the prediction time of the ETL tasks by using the time prediction equation, wherein step S22 comprises determining the prediction time of the ETL tasks, by using the time prediction equation, through the number of ETL tasks to be processed in a current stage and a data reading rate of the hospital center;

step S23: determining a priority of the ETL tasks by using the prediction time, wherein a shortest task priority principle is used to determine the priority, and the shortest task priority principle stipulates that a ETL task with shorter remaining processing time in the current stage has a higher priority to reduce average waiting time of all ETL tasks;

step S24: dispatching, by the dispatching machine, the ETL tasks to the executors for execution according to the priority of the ETL tasks;

step S241: initiating, by the dispatching machine, active task queues and expired task queues;

step S242: adding the ETL tasks to the active task queues according to the priority;

step S243: when the ETL tasks in the active task queues are empty, exchanging the active task queues and the expired task queues, and continuously performing, by the dispatching machine, distributing and dispatching from the active task queues;

step S3: collecting and counting up, by the dispatching machine, resource index vectors reported by each executor and resource demand vectors of ETL tasks to be dispatched in the current stage, and screening an executor set meeting resource demands of the ETL tasks to be dispatched;

step S4: calculating a current task load of each executor in the executor set;

step S5: selecting, by the dispatching machine, the executor with a minimum current task load to execute the ETL tasks according to the current task load of each executor; and step S6: adding, by the dispatching machine, the ETL tasks to executor active queues, determining the priority of the ETL tasks in the executor active queues according to prediction time determined by the prediction equation, and selecting, by the dispatching machine, the ETL tasks from the executor active queues according to the priority for execution;

in the ETL task execution process, setting an ETL task operation time threshold value, when the ETL task execution time is greater than or equal to the ETL task operation time threshold value, pausing execution of the ETL tasks, adding the ETL tasks to the executor expire queues, and waiting for next-time dispatching;

in the ETL task execution process, detecting ETL task stage information, when stages are switched, pausing execution of the ETL tasks, adding the ETL tasks to dispatching machine expired task queues, and waiting for re-dispatching by the dispatching machine; and in the ETL task execution process, when the executor active queues are empty after executor dispatching, exchanging the executor active queues and the executor expire queues, and continuously performing, by the dispatching machine, dispatching and execution from the executor active queues.

2. The medical ETL task dispatching method based on multiple centers according to claim 1, wherein step S3 comprises sub-steps of:

step S31: collecting and counting up, by the dispatching machine, resource index vectors of any executor;

step S32: collecting and counting up, by the dispatching machine, the resource demand vectors of the ETL tasks to be dispatched in the current stage; and step S33: screening the executor set meeting the resource demands of the ETL tasks to be dispatched by using the resource index vectors and the resource demand vectors.

3. The medical ETL task dispatching method based on multiple centers according to claim 1, wherein step S4 comprises sub-steps of:

step S41: calculating a sum of prediction time of all the ETL tasks in each executor active queue and each executor expire queue in each executor set by using the time prediction equation; and step S42: calculating current task loads corresponding to the executors through the sum of the prediction time and a collection of all the ETL tasks.

4. The medical ETL task dispatching method based on multiple centers according to claim 1, wherein when the current task loads of the plurality of executors are the same in step S5, the executor with a minimum value is screened out to perform dispatching and execution on the ETL tasks according to the resource index vectors of the executors in the current stage and the resource demand vectors of the ETL tasks in the current stage in combination with resource weight values of the executors.

5. The medical ETL task dispatching method based on multiple centers according to claim 4, wherein when the plurality of executors are screened out in step S5, one executor is randomly selected to perform dispatching and execution on the ETL tasks.

6. A system for implementing the medical ETL task dispatching method based on multiple centers according to claim 1, comprising:

a test module, configured to collect ETL task operation data and determine resource demands of ETL tasks and a time prediction equation;

a hospital center module, configured to deploy the ETL tasks and submit the ETL tasks to a dispatching machine module to perform dispatching and distributing of the ETL tasks;

the dispatching machine module, configured to calculate executor sources and task loads, to calculate task prediction time and determine a priority of the ETL tasks by using the time prediction equation, and to dispatch the ETL tasks to an executor module according to the priority; and the executor module, configured to execute the ETL tasks and perform overtime dispatching and stage switching dispatching on the ETL tasks.

7. A medical ETL task dispatching apparatus based on multiple centers, comprising a memory and one or more processors, wherein the memory stores an executor code, and when executing the executable code, the one or more processors are configured to implement the medical ETL task dispatching method based on multiple centers according to claim 1.

8. A non-transitory computer-readable storage medium, wherein a program is stored on the non-transitory computer-readable storage medium, and when the program is executed by a processor, the medical ETL task dispatching method based on multiple centers according to claim 1 is implemented.

* * * * *